(12) United States Patent
Gliner et al.

(10) Patent No.: US 10,722,306 B2
(45) Date of Patent: Jul. 28, 2020

(54) SYSTEM FOR TRACKING GUIDEWIRE WITH RAY TRACING CAPABILITY

(71) Applicant: Biosense Webster (Israel) Ltd., Yokneam (IL)

(72) Inventors: Vadim Gliner, Haifa (IL); Ram Bernard Mayer, Raanana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 642 days.

(21) Appl. No.: 15/289,813

(22) Filed: Oct. 10, 2016

(65) Prior Publication Data

US 2017/0135764 A1  May 18, 2017

Related U.S. Application Data

(60) Provisional application No. 62/256,304, filed on Nov. 17, 2015.

(51) Int. Cl.
*A61B 18/20* (2006.01)
*A61B 6/03* (2006.01)
(Continued)

(52) U.S. Cl.
CPC .............. *A61B 18/20* (2013.01); *A61B 5/062* (2013.01); *A61B 5/743* (2013.01); *A61B 6/032* (2013.01); *A61B 6/12* (2013.01); *A61B 6/5211* (2013.01); *A61B 6/547* (2013.01); *A61B 34/20* (2016.02); *A61M 25/09* (2013.01); *A61B 6/461* (2013.01);
(Continued)

(58) Field of Classification Search
CPC ........... A61B 6/032; A61B 6/12; A61B 6/461;
A61B 6/501; A61B 6/5211; A61B 6/547;
A61B 5/062; A61B 5/743; A61B 18/20;
A61B 18/22; A61B 2018/00327; A61B
2018/00577; A61B 2018/00589; A61B
2018/00625; A61B 2018/00642; A61B
2018/00708; A61B 2018/2015;
(Continued)

(56) References Cited

U.S. PATENT DOCUMENTS 5,638,819 A * 6/1997 Manwaring .......... A61B 1/0005
600/103
2007/0208252 A1   9/2007 Makower
(Continued)

OTHER PUBLICATIONS

European Search Report dated Apr. 19, 2017 for Application No. 16199073.4, 7 pages.
(Continued)

*Primary Examiner* — Boniface N Nganga
(74) *Attorney, Agent, or Firm* — Frost Brown Todd LLC

(57) ABSTRACT

A method, including registering a computerized tomography (CT) scan of a patient with a tracking system configured to track a location and an orientation of a sensor in the patient, and displaying the CT scan on a screen. The method further includes tracking coordinates of a probe having the sensor inside the patient using the tracking system. Based on the tracked coordinates, an icon representative of the location of the sensor is overlaid on the CT scan on the screen. The method also includes overlaying on the CT scan a ray, issuing from the icon in a direction corresponding to the orientation of the sensor, and traversing the screen to a termination point chosen responsively to a gray level distribution of the CT scan.

19 Claims, 5 Drawing Sheets

(51) Int. Cl.
 *A61B 6/12*   (2006.01)
 *A61M 25/09*  (2006.01)
 *A61B 6/00*   (2006.01)
 *A61B 5/00*   (2006.01)
 *A61B 5/06*   (2006.01)
 *A61B 34/20*  (2016.01)
 *A61B 18/00*  (2006.01)
 *A61B 34/10*  (2016.01)
 *A61B 90/30*  (2016.01)
 *A61B 34/00*  (2016.01)

(52) U.S. Cl.
 CPC ............... *A61B 6/501* (2013.01); *A61B 34/25* (2016.02); *A61B 2018/00327* (2013.01); *A61B 2018/00577* (2013.01); *A61B 2018/00625* (2013.01); *A61B 2018/00642* (2013.01); *A61B 2018/00708* (2013.01); *A61B 2034/104* (2016.02); *A61B 2034/2051* (2016.02); *A61B 2090/306* (2016.02)

(58) Field of Classification Search
 CPC ... A61B 34/20; A61B 34/25; A61B 2034/104; A61B 2034/2051; A61B 2090/306; A61M 25/09
 See application file for complete search history.

(56) References Cited

U.S. PATENT DOCUMENTS

| | | | |
|---|---|---|---|
| 2011/0190662 A1* | 8/2011 | McWeeney | A61B 10/04 600/567 |
| 2011/0196355 A1* | 8/2011 | Mitchell | A61B 18/22 606/11 |
| 2014/0142425 A1 | 5/2014 | Razzaque et al. | |
| 2016/0007842 A1 | 1/2016 | Govari et al. | |
| 2016/0038247 A1* | 2/2016 | Bharadwaj | G06F 3/04847 600/426 |

OTHER PUBLICATIONS

U.S. Appl. No. 62/209,946, entitled "Automatic ENT Surgery Preplanning Using a Backtracking Maze Problem Solution," filed Aug. 26, 2015.

U.S. Appl. No. 62/221,367, entitled "Adding a Tracking Sensor to a Rigid Tool," filed Sep. 21, 2015.

\* cited by examiner

SYSTEM FOR TRACKING GUIDEWIRE WITH RAY TRACING CAPABILITY

CROSS-REFERENCE TO RELATED APPLICATION

This application claims the benefit of U.S. Provisional Patent Application 62/256,304, filed 17 Nov. 2015, which is incorporated herein by reference.

FIELD OF THE INVENTION

The present invention relates generally to surgery, and specifically to nasal sinus laser surgery.

BACKGROUND OF THE INVENTION

Laser surgery uses a laser beam to ablate or vaporize tissue, rather than cutting the tissue with a scalpel.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

registering a computerized tomography (CT) scan of a patient with a tracking system configured to track a location and an orientation of a sensor in the patient;

displaying the CT scan on a screen;

tracking coordinates of a probe including the sensor inside the patient using the tracking system;

based on the tracked coordinates, overlaying on the CT scan on the screen an icon representative of the location of the sensor; and overlaying on the CT scan a ray, issuing from the icon in a direction corresponding to the orientation of the sensor, and traversing the screen to a termination point chosen responsively to a gray level distribution of the CT scan.

In an alternative embodiment the gray level distribution is indicative of a local tissue density in the CT scan.

In a further alternative embodiment overlaying the ray includes terminating the ray at a pixel where a gray level value of the displayed CT scan crosses a predefined threshold.

In a yet further alternative embodiment the method includes directing laser radiation from the probe, in response to overlaying the ray to the termination point, to a location of a desired ablation target in the patient corresponding to the termination point.

In a disclosed embodiment the tracking system includes a magnetic tracking system.

In a further disclosed embodiment the CT scan includes a CT scan of nasal sinuses of the patient, and the probe consists of a guidewire configured and dimensioned to be inserted into the nasal sinuses.

There is further provided, according to an embodiment of the present invention, apparatus, including:

a screen configured to display a computerized tomography (CT) scan of a patient;

a probe having a sensor configured to be inserted into the patient;

a tracking system configured to track a location and an orientation of the sensor; and a processor, configured to:

register the CT scan with the tracking system, track coordinates of the probe using the tracking system, based on the tracked coordinates, overlay on the CT scan on the screen an icon representative of the location of the sensor, and overlay on the CT scan a ray, issuing from the icon in a direction corresponding to the orientation of the sensor, and traversing the screen to a termination point chosen responsively to a gray level distribution of the CT scan.

The present disclosure will be more fully understood from the following detailed description of the embodiments thereof, taken together with the drawings, in which:

DETAILED DESCRIPTION OF EMBODIMENTS

Overview

Figure 1:
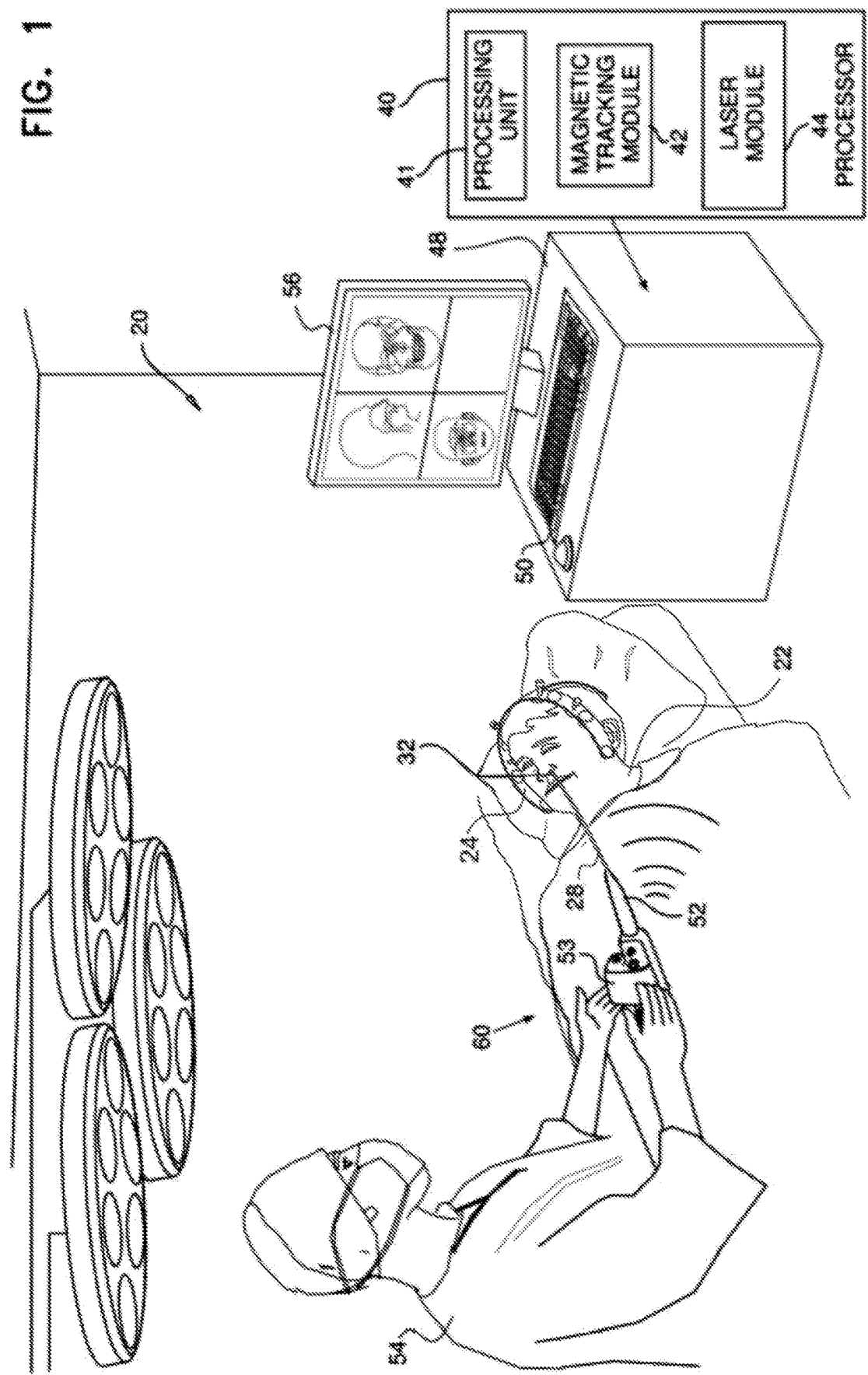
FIG. 1 is a schematic illustration of a laser surgery system, according to an embodiment of the present invention.

Laser radiation may be used to ablate tissue in a nasal sinus surgery procedure. However, the laser radiation needs to be correctly targeted, since incorrect targeting may cause trauma to healthy tissue. Embodiments of the present invention provide a physician with a system that is able to verify that the laser radiation will be correctly targeted, prior to actual irradiation of a patient in the procedure.

Prior to performance of the procedure, a computerized tomography (CT) scan of the patient's head is acquired. At the beginning of the procedure, magnetic field generators are positioned around the patient's head. The field from the generators generates signals in a magnetic sensor in the field, and the signals are used to track the location and orientation of the sensor. The sensor is incorporated into the distal end of a probe, herein assumed to comprise a guidewire, used for the procedure. The guidewire also has a fiber optic threaded from the proximal end of the guidewire to the distal end, and a laser is coupled to the proximal end of the fiber optic.

For the procedure, the CT scan is displayed to the physician on a screen. The physician inserts the guidewire into the patient's nostril and a system processor displays on the CT scan an icon representative of the position of the sensor, corresponding to the position of the distal end of the guidewire. The physician uses the icon to move the guidewire to a desired position proximate to a marker on the scan, the marker corresponding to a site in the patient to be ablated.

In the desired position, the physician may activate the system processor to display on the CT scan a virtual ray emanating from the icon, in a direction defined by the orientation of the distal end of the guidewire. The processor is configured to continue the virtual ray according to the gray levels of the CT scan. I.e., the ray is typically configured to traverse black or almost black regions of the scan, but to terminate on hitting lighter gray levels. (The black and almost black levels correspond to regions such as air that do not impede radiation from the proximal end laser. The lighter gray levels typically correspond to tissue that it is undesirable to radiate.)

When the virtual ray is shown on the CT scan as reaching the marker, verifying to the physician that there is no obstruction from the icon to the marker, the physician may activate the system processor to toggle the laser on. Toggling of the laser on ablates the target represented by the marker.

Thus, in an embodiment of the present invention a CT scan of a patient is registered with a tracking system, typically a magnetic tracking system, that is able to track a location and orientation of a sensor in the patient. The CT scan is displayed on a screen, and a processor tracks coordinates of a probe, comprising the sensor, that is inserted into the patient using the tracking system. Based on the tracked coordinates, the processor overlays on the CT scan on the screen an icon representative of the location of the sensor. In addition, the processor overlays on the CT scan a ray, issuing from the icon in a direction corresponding to the orientation of the sensor. The ray is traversed on the screen to a termination point chosen responsively to a gray level distribution of the CT scan.

Once the ray traverses to the termination point, laser radiation may be directed from the probe, to a location of a desired ablation target in the patient corresponding to the termination point.

DETAILED DESCRIPTION

Reference is now made to FIG. 1, which is a schematic illustration of a laser surgery system 20, according to an embodiment of the present invention. System 20 is typically used during an invasive procedure where a laser is operated to ablate a portion of a nasal sinus of a patient 22, and the system includes a probe 28, typically in the form of a guidewire and also referred to herein as guidewire 28, that is used in the system, as described in more detail below.

Prior to the procedure, typically a number of days beforehand, a computerized tomography (CT) scan of the head of patient 22 is made. The data from the CT scan is stored for use by a system processor 40, which operates system 20.

Figure 2:
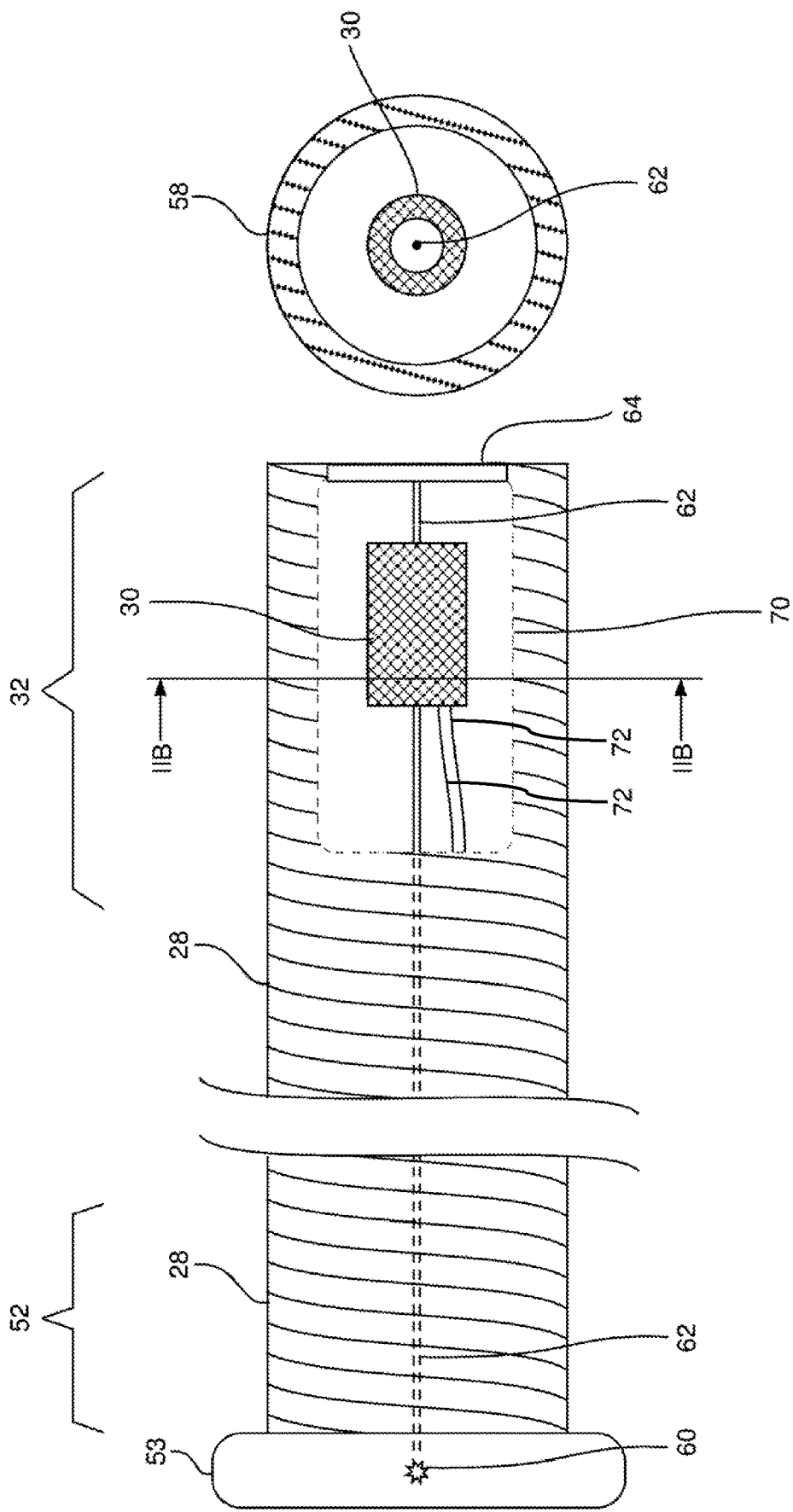
FIG. 2A is a schematic longitudinal illustration of a guidewire.
FIG. 2B is a schematic cross-section of the guidewire, according to an embodiment of the present invention.

For the actual procedure, a set of magnetic field generators 24, shown in FIG. 1 in schematic form, are placed in proximity to the head of the patient. As is described in more detail below and as shown in FIGS. 2A-2B, guidewire 28 comprises a magnetic field sensor 30 at its distal end 32, and the field from generators 24 enables the location and orientation of the sensor, and thus of the guidewire distal end coordinates, to be tracked, after the distal end has been inserted into the nasal sinus of the patient. A system using magnetic field generators, such as generators 24, for tracking a sensor inserted into a patient is described in U.S. patent application Ser. No. 14/792,823, published as U.S. Pub. No. 2016/0007842 on Jan. 14, 2016, to Govari et al., in U.S. Provisional Patent Application 62/209,946, to Gliner, and in U.S. Provisional Patent Application 62/221,367, also to Gliner, which are incorporated herein by reference. In addition, the Carto® system produced by Biosense Webster, of Diamond Bar, Calif., uses a tracking system similar to that described herein for finding the location and orientation of a coil in a region irradiated by magnetic fields.

For clarity and simplicity, the present application assumes that sensor 30 is a magnetic field sensor, which is tracked by a magnetic tracking system comprising generators 24. However, it will be appreciated that other types of sensors and other types of tracking systems, for sensor 30, may be used, and those having ordinary skill in the art will be able to adapt the application, mutatis mutandis, for the other types of sensors and tracking systems. Thus, the scope of the present invention comprises these other types of sensors and tracking systems.

Elements of system 20 may be controlled by a system processor 40, comprising a processing unit (PU) 41 communicating with one or more modules such as a magnetic tracking module 42, which enables the processing unit to control generators 24 and to track sensor 30. The processing unit may also communicate with a laser module 44, the function of which is described below.

Generators 24 define a generator frame of reference, and the location and orientation coordinates of sensor 30 are determined with respect to this frame of reference. At the beginning of the procedure the CT scan of the patient's head is registered with the generator frame of reference. For example, the CT scan comprises the nasal tip of the patient, and other external features such as a point between the eyebrows. To register the CT scan with the generator frame of reference an operator of system 20 may place a wand tip, having a sensor similar to sensor 30, on specific external features that are present in the CT scan. PU 41, using module 42, may find the positions of the specific external features in the generator frame of reference, and for the registration, form a correspondence between these positions and the locations of the features in the CT scan. However, any other convenient method of registration between the tracking system used and the CT scan, that is known in the art, may be used.

Processor 40 may be mounted in a console 48, which comprises operating controls 50 that typically include a keypad and/or a pointing device such as a mouse or trackball. Console 48 also connects to other elements of system 20, such as a proximal end 52 of guidewire 28 and to a laser 60 mounted in a proximal end holder 53 of the guidewire. A physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

FIG. 2A is a schematic longitudinal illustration of guidewire 28, and FIG. 2B is a schematic cross-section of the guidewire taken along a line IIB-IIB, according to an embodiment of the present invention. Guidewire 28 is typically formed as a coil 58 of stainless steel wire, and in one embodiment has an outside diameter of 0.9 mm. However, the guidewire of other embodiments of the present invention may have outer diameters that are greater than or less than 0.9 mm.

A fiber optic 62 is threaded through coil 58, and terminates at, typically by being cemented to, a window 64 fixed at the distal end of the guidewire. The fiber optic terminates at proximal end 52 of the guidewire, and laser 60 is mounted at the proximal end termination of the fiber optic so that, when energized, the laser directs laser radiation into the fiber optic. Typically optical elements are used to direct the energy into the fiber optic, but for simplicity such elements are not shown in the figure.

A cutaway section 70 of distal end 32 shows internal elements of the distal end. Field sensor 30 is fixedly attached to the interior of the distal end. The field sensor is typically a single axis coil having an axis of symmetry parallel to, and typically coincident with, the axis of symmetry of coil 58, and fiber optic may be threaded through the interior of the single axis coil.

Conductive wires 72 transfer signals, generated by sensor 30 in response to the magnetic fields from generators 24 passing through the sensor, to processor 40. Alternatively, the signals may be transferred wirelessly to processor 40. From the acquired signals, the processor is able to calculate the orientation and location of sensor 30, and thus of distal end 32.

Figure 3:
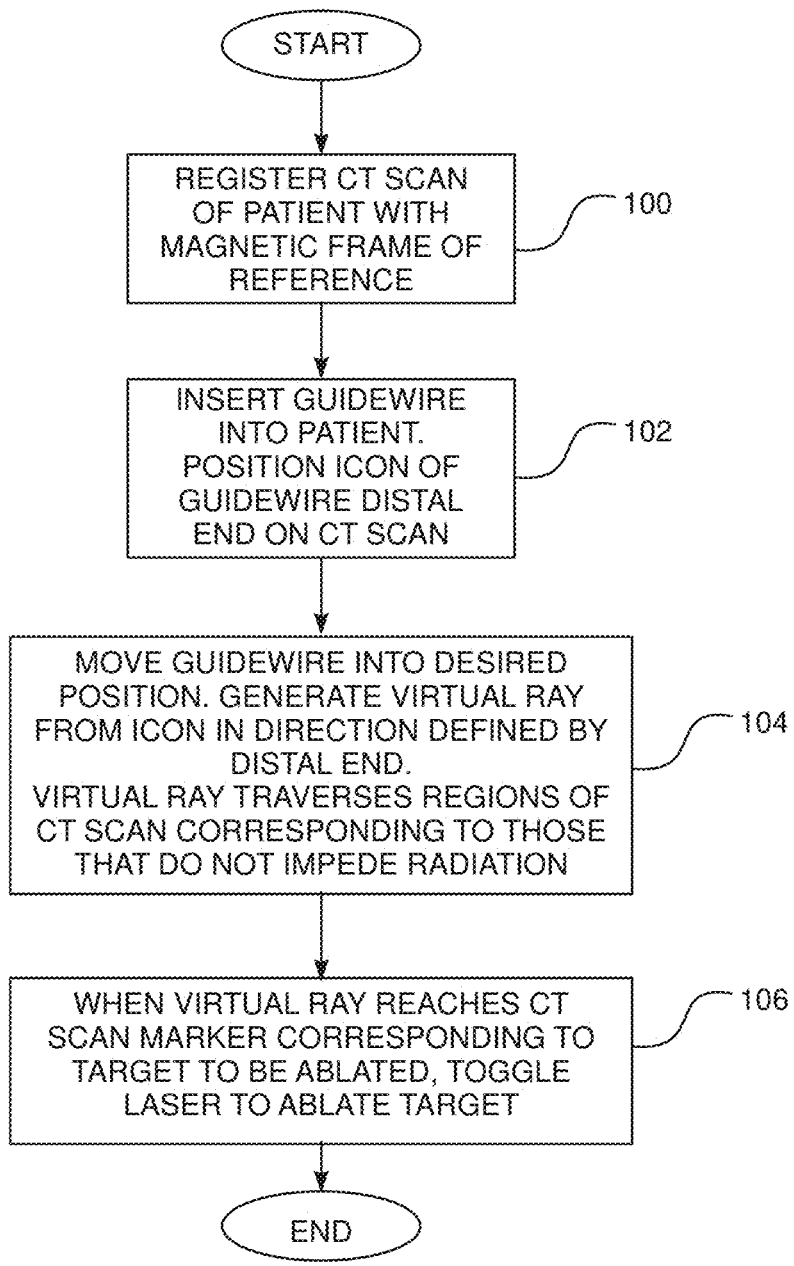
FIG. 3 is a flowchart of steps performed in operation of the laser surgery system, according to an embodiment of the present invention.
Figure 4:
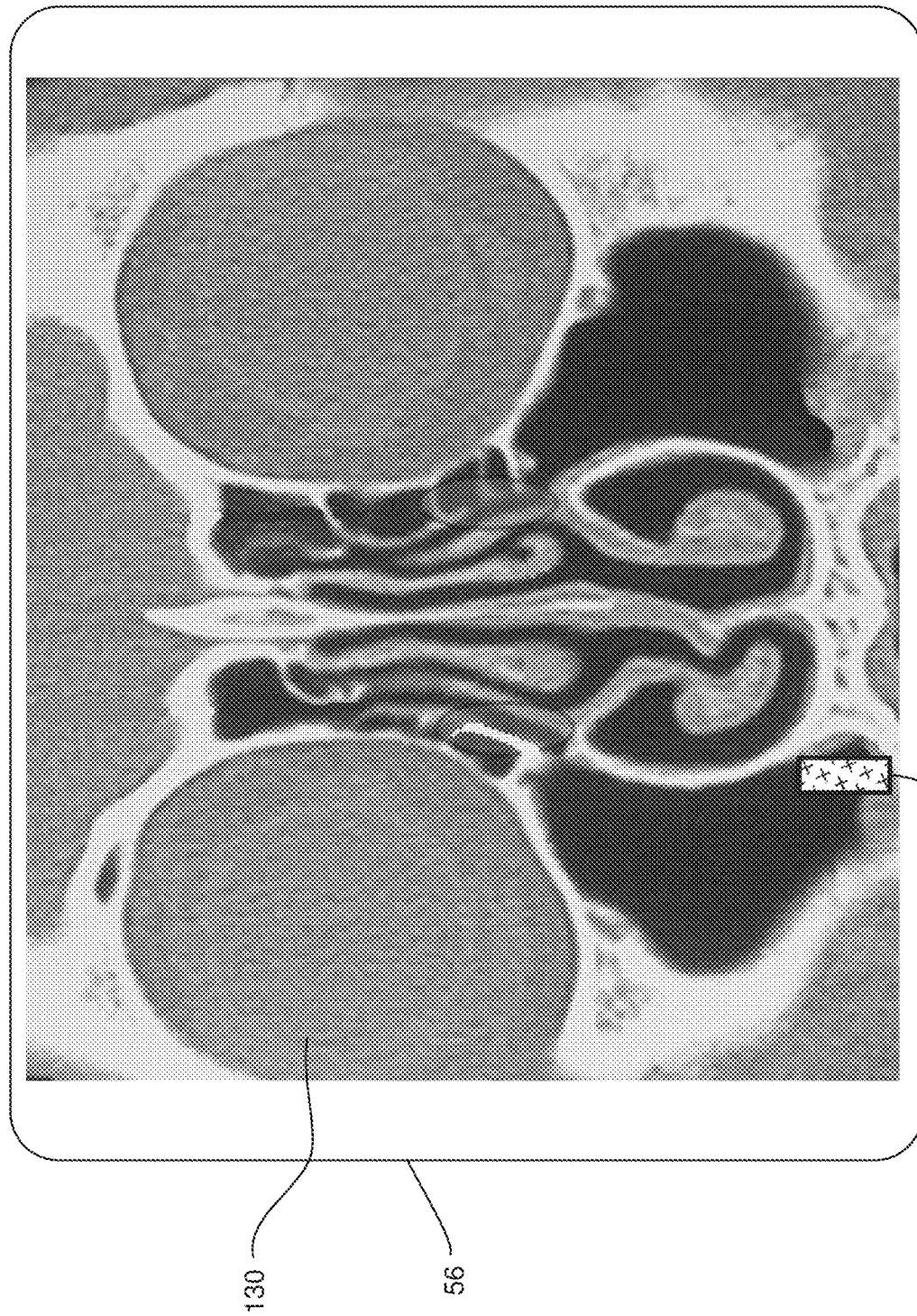
FIGS. 4 and 5 are schematic diagrams illustrating some of the steps of the flowchart, according to embodiments of the present invention.
Figure 5:
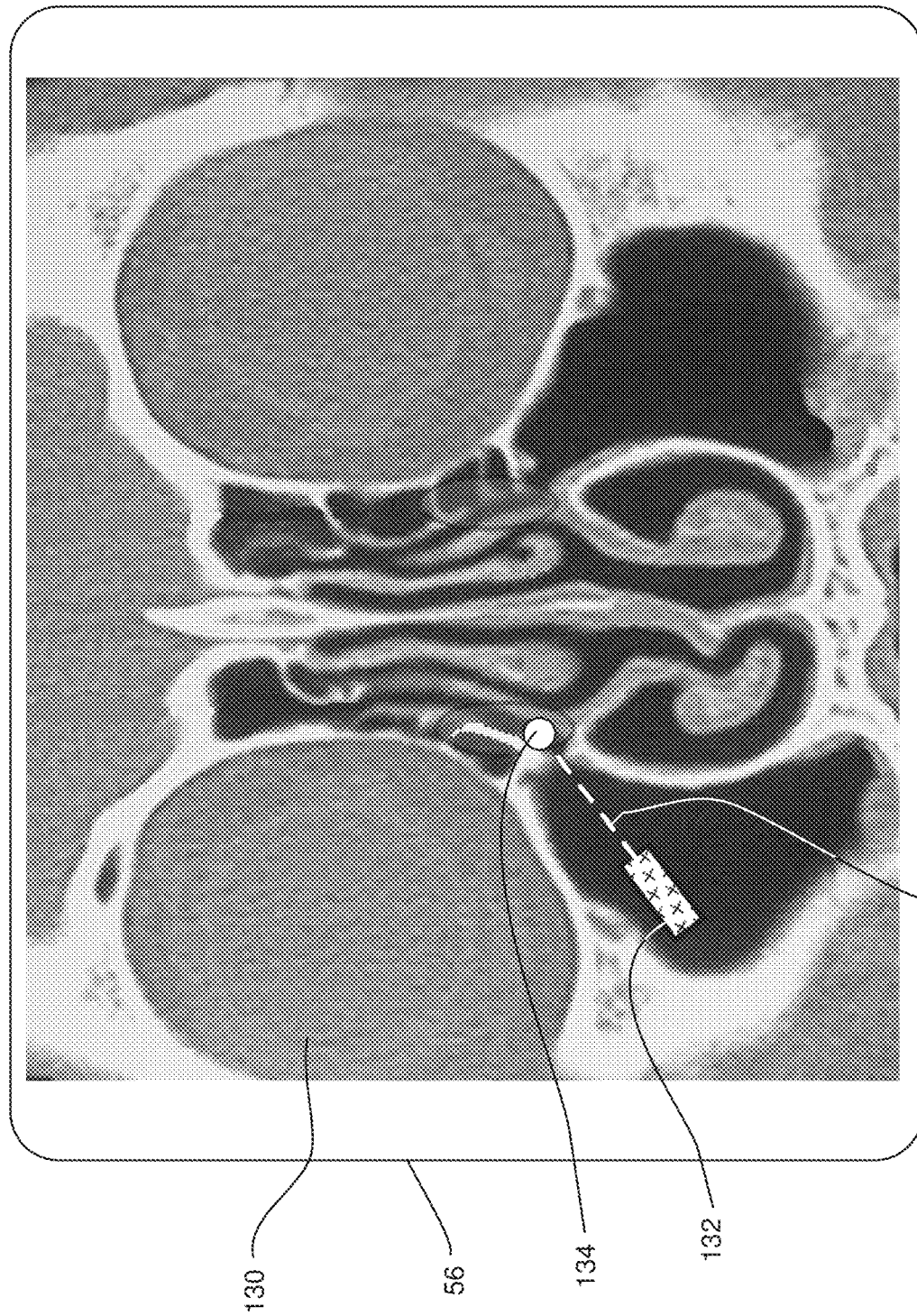

FIG. 3 is a flowchart of steps performed in operation of system 20, and FIGS. 4 and 5 are schematic diagrams illustrating some of the steps, according to embodiments of the present invention. In a preparatory step 100, a CT scan of patient 22 is performed and the scanned image of the patient is registered with the frame of reference defined by generators 24, as is described above. FIG. 4 illustrates a schematic CT scan 130 of the patient, which is presented on screen 56.

In an initial procedure step 102, physician 54 inserts guidewire 28 into a nostril of patient 22, and processor 40 uses signals from sensor 30 to acquire and track the location and orientation of distal end 32. The processor overlays an icon 132, representative of the location and orientation of distal end 32, on scan 130, using the registration performed in step 100. FIG. 4 illustrates icon 132 on scan 130 for step 102.

In a continuing procedure step 104 the physician moves guidewire 28, and so icon 132, to a desired position proximate to a marker 134 on the scan, the marker corresponding to a site in the patient to be ablated. In the desired position, the physician activates system 20 so that processor 40 overlays on scan 130 a virtual ray 136 emanating from icon 132, in a direction defined by the orientation of distal end 32.

Processor 40 is configured to continue virtual ray 136 according to the gray levels of the CT scan. I.e., the ray is typically configured to traverse black or almost black regions of the scan, but to terminate at a particular pixel of the scan on hitting lighter gray levels. The black and almost black levels correspond to regions such as air that do not impede radiation from laser 60. The actual gray levels that the virtual ray may traverse, and the levels it may not traverse, may be set as predefined thresholds prior to the procedure by physician 54, and these levels may be determined without undue experimentation. It will be understood that the gray levels of the CT scan are indicative of a local tissue density.

FIG. 5 illustrates virtual ray 136 as reaching marker 134, since the ray does not traverse lighter gray levels of the scan.

In an operational step 106, once virtual ray 136 is shown on scan 130 as reaching marker 134, the physician may use controls 50, and/or controls in holder 53, to toggle laser 60 on. Toggling of the laser on ablates the target represented by marker 134.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
   registering a computerized tomography (CT) scan of a patient with a tracking system, the tracking system comprising a processor configured to track a location and an orientation of a sensor in the patient and a field generator;
   displaying the CT scan on a screen;
   operating the field generator to produce a field configured to interact with the sensor and indicate a location and orientation of the sensor within the field;
   tracking coordinates of a probe comprising the sensor inside the patient using the tracking system;
   based on the tracked coordinates, overlaying on the CT scan on the screen an icon representative of the location of the sensor;
   overlaying on the CT scan a ray, issuing from the icon in a direction corresponding to the orientation of the sensor, and traversing the screen to a termination point chosen responsively to a gray level distribution of the CT scan at the termination point; and
   updating the icon representative of the location of the sensor, the direction of the ray, and the termination point of the ray in response to a change in the location or orientation of the sensor.

2. The method according to claim 1, wherein the CT scan comprises at least one substantially black portion and at least one non-black portion, and wherein the gray level distribution is indicative of a local tissue density in the CT scan.

3. The method according to claim 1, further comprising setting a predefined threshold that indicates a set of gray levels that cannot be traversed by the ray and a set of gray levels that can be traversed by the ray, and wherein overlaying the ray comprises terminating the ray at a pixel where a gray level value of the displayed CT scan crosses the predefined threshold.

4. The method according to claim 1, and comprising directing laser radiation from the probe, in response to overlaying the ray to the termination point, to a location of a desired ablation target in the patient corresponding to the termination point.

5. The method according to claim 1, wherein the tracking system comprises a magnetic tracking system and the field generator comprises a magnetic field generator.

6. The method according to claim 1, wherein the CT scan comprises a CT scan of nasal sinuses of the patient, and wherein the probe comprises a guidewire configured and dimensioned to be inserted into the nasal sinuses.

7. Apparatus, comprising:
   a screen configured to display a computerized tomography (CT) scan of a patient;
   a probe comprising a sensor configured to be inserted into the patient;
   a tracking system comprising a processor configured to track a location and an orientation of the sensor and a field generator; and
   the processor is configured to:
   receive the CT scan;
   register the CT scan with the tracking system,
   operate the field generator to produce a field configured to interact with the sensor and indicate a location and orientation of the sensor within the field,
   track coordinates of the probe using the tracking system,
   based on the tracked coordinates, overlay on the CT scan on the screen an icon representative of the location of the sensor, overlay on the CT scan a ray, issuing from the icon in a direction corresponding to the orientation of the sensor, and traversing the screen to a termination point chosen responsively to a gray level distribution of the CT scan at the termination point, and update the icon representative of the location of the sensor, the direction of the ray, and the termination point of the ray in response to a change in the location or orientation of the sensor.

8. The apparatus according to claim 7, wherein the CT scan comprises at least one substantially black portion and at least one non-black portion, and wherein the gray level distribution is indicative of a local tissue density in the CT scan.

9. The apparatus according to claim 7, wherein the processor is configured to receive a predefined threshold that indicates a set of gray levels that cannot be traversed by the ray and a set of gray levels that can be traversed by the ray, and wherein overlaying the ray comprises terminating the ray at a pixel where a gray level value of the displayed CT scan crosses the predefined threshold.

10. The apparatus according to claim 7, and comprising a laser which directs laser radiation from the probe, in response to overlaying the ray to the termination point, to a location of a desired ablation target in the patient corresponding to the termination point.

11. The apparatus according to claim 7, wherein the tracking system comprises a magnetic tracking system and the field generator comprises a magnetic field generator.

12. The apparatus according to claim 7, wherein the CT scan comprises a CT scan of nasal sinuses of the patient, and wherein the probe comprises a guidewire configured and dimensioned to be inserted into the nasal sinuses.

13. A system comprising:
    (a) a probe comprising a magnetic sensor;
    (b) a magnetic tracking system operable to produce a magnetic field that interacts with the magnetic sensor to produce a set of tracking data;
    (c) a display;
    (d) a processor configured to:
        (i) receive a CT scan and register the CT scan with the magnetic tracking system,
        (ii) operate the magnetic tracking system and determine a location and an orientation of the magnetic sensor within the magnetic field based on the set of tracking data,
        (iii) display the CT scan on the display,
        (iv) render an icon representative of the location and orientation of the sensor on the CT scan,
        (v) render a virtual ray on the CT scan that:
            (A) originates from the icon,
            (B) extends in a direction corresponding to the orientation of the sensor, and
            (C) terminates at a termination point, wherein the termination point corresponds to a point of the CT scan that is associated with a tissue density that is above a set predefined threshold, and
        (vi) update the icon and the virtual ray in response to a change in the location or orientation of the magnetic sensor.

14. The system of claim 13, wherein the preconfigured threshold is associated with a tissue density that does not impede laser radiation.

15. The system of claim 13, further comprising a laser operable to direct laser radiation from the probe along a laser axis, wherein the processor is further configured to render the virtual ray on the CT scan so that a virtual ray axis of the virtual ray matches the laser axis.

16. The system of claim 13, wherein the processor is further configured to:
    (i) receive data identifying a site of the CT scan that is associated with a tissue ablation, and
    (ii) render a marker on the CT scan at the site.

17. The system of claim 16, wherein the processor is further configured to determine the termination point as the marker when the virtual ray intersects the marker.

18. The system of claim 17, wherein the processor is further configured to, once the termination point is determined as the marker, allow a user of the probe to operate a laser to direct laser radiation from the probe.

19. The system of claim 18, wherein the processor is further configured to render the virtual ray on the CT scan so that a virtual ray axis of the virtual ray matches a laser axis of the laser.

* * * * *